United States Patent [19]

Kato et al.

[11] Patent Number: 4,668,375

[45] Date of Patent: May 26, 1987

[54] ELECTRIC CONNECTION TERMINAL FOR A SENSOR ELEMENT UTILIZING CERAMICS

[75] Inventors: Nobuhide Kato, Aichi; Takao Murase, Konan, both of Japan

[73] Assignee: NGK Insulators, Ltd., Japan

[21] Appl. No.: 791,538

[22] Filed: Oct. 25, 1985

[30] Foreign Application Priority Data

Nov. 1, 1984 [JP] Japan .............................. 59-228875

[51] Int. Cl.⁴ .......................................... G01N 27/46
[52] U.S. Cl. ................... 204/426; 204/425; 204/427; 339/278 C; 361/411; 200/268; 200/269
[58] Field of Search .................. 204/1 S, 421–429; 339/278 R, 278 C; 361/411; 200/265, 268, 269

[56] References Cited

U.S. PATENT DOCUMENTS

| | | | |
|---|---|---|---|
| 3,781,596 | 12/1973 | Galli et al. | 361/411 |
| 3,843,400 | 10/1974 | Radford et al. | 204/427 |
| 3,934,336 | 1/1976 | Morse | 361/411 |
| 4,225,634 | 9/1980 | Tanaka et al. | 204/429 |
| 4,257,863 | 3/1981 | Hoffman | 204/429 |
| 4,505,807 | 3/1985 | Yamada | 204/428 |

Primary Examiner—T. Tung
Attorney, Agent, or Firm—Parkhurst & Oliff

[57] ABSTRACT

An electric connection terminal arranged at a rear end of a sensor element and capable of affording quick and easy connection of the sensor element with a contacting element connected to a lead wire extending into a connector socket or connector insulator accommodating the contacting element for transmitting a signal detected at the front end of the sensor element, is composed of at least two conductive layers, and at least the lowermost layer of the conductive layers is composed of a mixture of a conductive metal and ceramics and/or glass, so that the layers bond firmly with each other and the lowermost layer bonds most firmly to the sensor element, whereby peeling-off of the connection terminal from the sensor element due to friction thereof against the contacting element and repetition of heating and cooling of the sensor element is eliminated.

9 Claims, 8 Drawing Figures

FIG.6
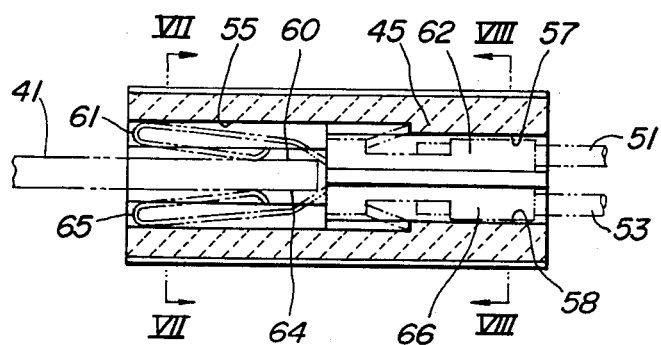
FIG.7
FIG.8
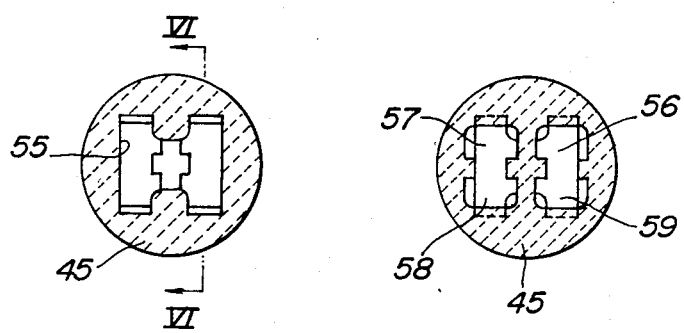

ELECTRIC CONNECTION TERMINAL FOR A SENSOR ELEMENT UTILIZING CERAMICS

BACKGROUND OF THE INVENTION

1. Field of the Invention

The present invention relates to an improvement of an electric connection terminal for a sensor element using ceramics, such as an oxygen sensor or the like which can be used for detecting an oxygen concentration in an exhaust gas of an automobile engine.

2. Related Art Statement

Heretofore, as an oxygen sensor for detecting an oxygen concentration in a substance to be detected such as an exhaust gas of an automobile engine or the like, a sensor has been proposed of a structure wherein each electrode layer is provided on both surfaces of a distal end of an elongated flat sensor substrate late consisting mainly of zirconia, one electrode being exposed to a standard substance such as air, the other electrode being exposed to a substance to be detected such as an exhaust gas, and an electromotive force produced between the two electrodes by the principle of an oxygen concentration cell is used as a detected signal.

This type of oxygen sensor has generally, a connection terminal for connecting a plurality of covered lead wires at the rear end of the sensor substrate, and the covered lead wires connected to the connection terminal for transmitting the detected signal to the outer circuit as an output.

Soldering of the covered lead wires one by one to the connection terminal of the sensor substrate is not efficient. Even when the covered lead wires are connected by a suitable caulking element to auxiliary lead wires extending from the connection terminal, the work of caulking is difficult and not efficient. Therefore, in order to solve the problem of electric connection of the sensor element with the covered lead wires, the inventors have previously proposed an oxygen sensor as Japanese Utility Model Applicaton Laid-open No. 150,449/85, which was laid-open to the public on Oct. 5, 1985, which is after the priority date of the above-identified application (Japanese Utility Model Application No. 38,406/84, U.S. patent application Ser. No. 709,802, now U.S. Pat. No. 4,588,494. FIG. 5 of the attached drawings shows a longitudinal cross-sectional view of the whole structure of the oxygen sensor with reference numeral 40.

Explaining FIG. 5 in detail, a sensor element 41 composed of an oxygen ion conductive solid electrolyte plate and two electrodes, etc., is accommodated in a cylindrical metallic protective tube 42 in such a fashion that the distal end 44 provided with the electrodes becomes the lower portion of the sensor element 41. The intermediate portion of the sensor element 41 is supported by an insulating porcelain 43. The upper end of the sensor element 41 is supported by a connector porcelain 45. The sensor element 41 is fixed in the protective tube 42 by means of cement, talc, glass or the like filler 46 filled above and below the insulating porcelain 43.

The protective tube 42 has many perforation holes 47 at its lower end so that the measuring electrode arranged at the outer surface of the lower end of the sensor element 41 comes into contact with a gas atmosphere to be detected.

The protective tube 42 has at its upper end an earth lead wire 50 contacting the inner wall of the protective tube 42 and lead wires 51–53 inserted through a rubber stopper 48. The connector insulator 45 assumes a cylindrical shape, and has as its lower portion an insertion hole 55 for inserting the upper end of the sensor element 41, and at its upper portion lead wire insertion holes 56–59 for inserting the lead wires 50–53 which communicate with the insertion hole 55, as shown in the attached FIGS. 7 and 8. The lead wires 50–53, which are inserted into the lead wire insertion holes 56–59, are fixed at their ends by means of caulking metallic fittings 62, 66 which are integrally formed with folded resilient contacting elements 61, 65, as shown in the attached FIG. 6.

The contacting elements 61, 65 contact under pressure with the sensor element 41 which is inserted into the insertion hole 55 of the connector porcelain 45, so that they contact with connection terminals 60, 64 arranged at the surfaces of the end of the sensor element 41.

The lead wires are four in number in the illustrated structure, because the oxygen sensor 40 is provided with a heater so that the heater is arranged integrally with the sensor element 41 and two lead wires are necessary for supplying electric current to the heater from an electric power source.

In this way, the connector porcelain 45 functions as a connector socket, so that the connection between the lead wires 50–53 and the connection terminals 60, 64 of the sensor element 41 is facilitated.

However, the above connection terminals 60, 64 arranged on the sensor element 41 have hitherto been fixed on the sensor element 41 by baking a film of a metal such as nickel, gold, silver or platinum, etc. on surfaces of a plane plate of a solid electrolyte, so that they have a drawback in that the bonding force of the terminals to the sensor element is not strong. For instance, when the oxygen sensor 40 is mounted on an automobile, there is a drawback in that the connection terminals 60, 64 are peeled off from the sensor element 41 by friction thereof against the contacting elements 61, 65 due to vibration of the automobile and repetition of heating and cooling of the sensor element 41.

SUMMARY OF THE INVENTION

It is an object of the present invention to obviate the above-mentioned drawback of prior connection terminals of a sensor element.

Another object of the present invention is to provide an electric connection terminal which is arranged at one end of a sensor substrate composed mainly of ceramics and which is inserted together with the end of the sensor substrate into a separate connector socket for electrical connection with s contacting element in the connector socket, comprising at least two thick or thin conductive layers laminated on the sensor substrate, at least the lowermost layer of the conductive layers contacting the sensor substrate being composed of a mixture of a conductive metal and at least one of ceramics and glass.

Because the lowermost layer of the electric connection terminal contains ceramics, glass or a mixture thereof, it exhibits a much improved bonding force when it is fixed by baking on a sensor substrate composed mainly of ceramics. If an upper layer which is arranged on the lowermost layer has a larger content of conductive metal than the lowermost layer or if the upper layers which are arranged on the lowermost layer have larger contents of conductive metal than the lowermost layer with the increase of the upper layer, contact resistance between the uppermost layer of the conductive layers and the contacting element of the connector socket can be decreased.

The conductive layers are bonded firmly with each other, when they contain ceramics, glass or a mixture thereof.

Other objects and advantages of the present invention will be apparent from the ensuing descriptions and claims.

BRIEF DESCRIPTION OF THE DRAWINGS

For a better understanding of the present invention, reference is made to the accompanying drawings, in which:

FIG. 6 is a longitudinal crosssectional view of a connector porcelain of the oxygen sensor of FIG. 5 showing a crosssection of a connector porcelain of FIG. 7 taken along the line VI—VI;

FIG. 7 is a crosssectional view of the connector porcelain of FIG. 6 taken along the line VII—VII; and FIG. 8 is a crosssectional view of the connector porcelain of FIG. 6 taken along the line VIII—VIII.

Figure 1:
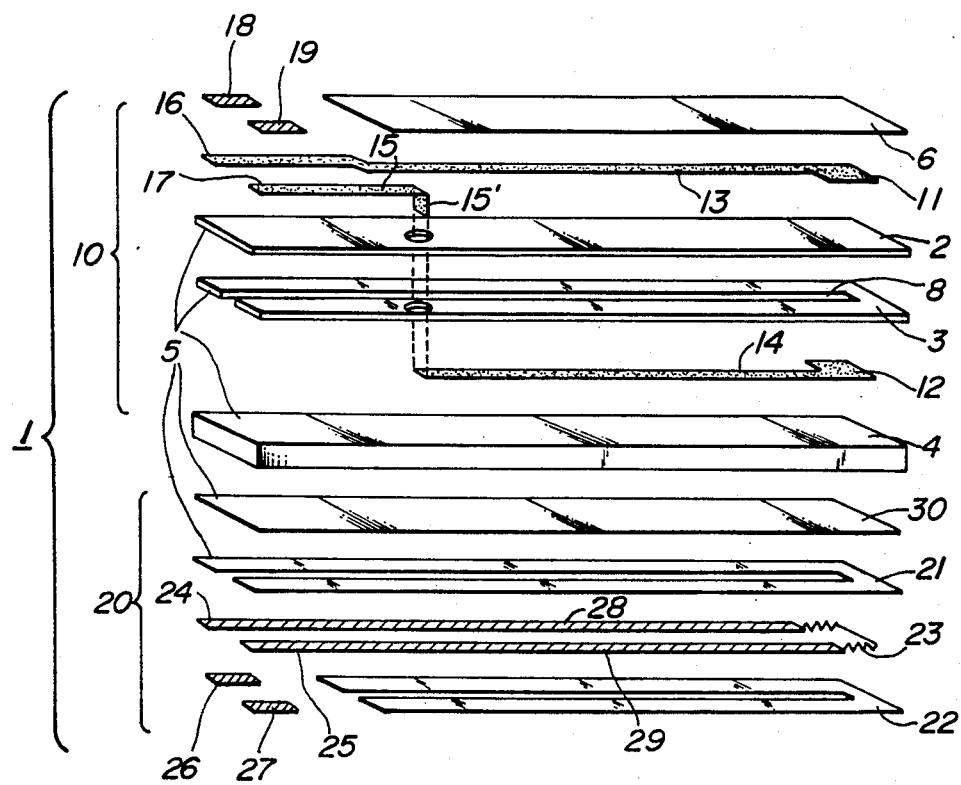
FIG. 1 is a schematic exploded perspective view of a sensor element showing a structure of an embodiment of the present invention.

Throughout different view of the drawings, the reference numerals indicate the following:

1 . . . sensor element, 2, 3 and 4 . . . solid electrolyte plates, 2a and 3a . . . throughholes, 5 . . . sensor substrate, 6 . . . protective layer, 7 . . . window, 8 . . . slit, 10 . . . sensor part of the sensor element 1, 11 . . . measuring electrode, 12 . . . standard electrode, 13, 14 and 15 . . . electrode leads, 15' . . . bend end portion, 16 and 17 . . . ends of electrode leads, 18 and 19 . . . upper layers of connecton terminals, 20 . . . heater part of the sensor element 1, 21 and 22 . . . insulating ceramics layers, 23 . . . heater, 24 and 25 . . . ends of heater leads, 26 and 27 . . . upper layers of connection terminals, 28 and 29 . . . heater leads, 30 . . . insulating layer, 31, 32, 33 and 34 . . . lower layers of connection terminals, 40 . . . oxygen sensor, 41 . . . sensor elements, 42 . . . metallic protective tube 43 . . . insulating porcelain, 44 . . . lower end of the sensor element 41, 45 . . . connector porcelain, 46 . . . filler, 47 . . . perforation hole, 48 . . . rubber stopper, 50 . . . earth lead wire, 51, 52 and 53 . . . lead wires, 55 . . . insertion hole for inserting an end of the sensor element 41, 56, 57, 58 and 59 . . . insertion holes for inserting the lead wires 50, 51, 52, and 53, 60 and 64 . . . connection terminals of the sensor element 41, 61 and 65 . . . resilient contacting elements, 62 and 66 . . . metal fittings for fixing the edges of the lead wires 51 and 53.

DETAILED DESCRIPTION OF THE PREFERRED EMBODIMENTS

Hereinafter, the present invention will be explained in more detail with reference to the attached drawings.

EXAMPLE 1

Figure 5:
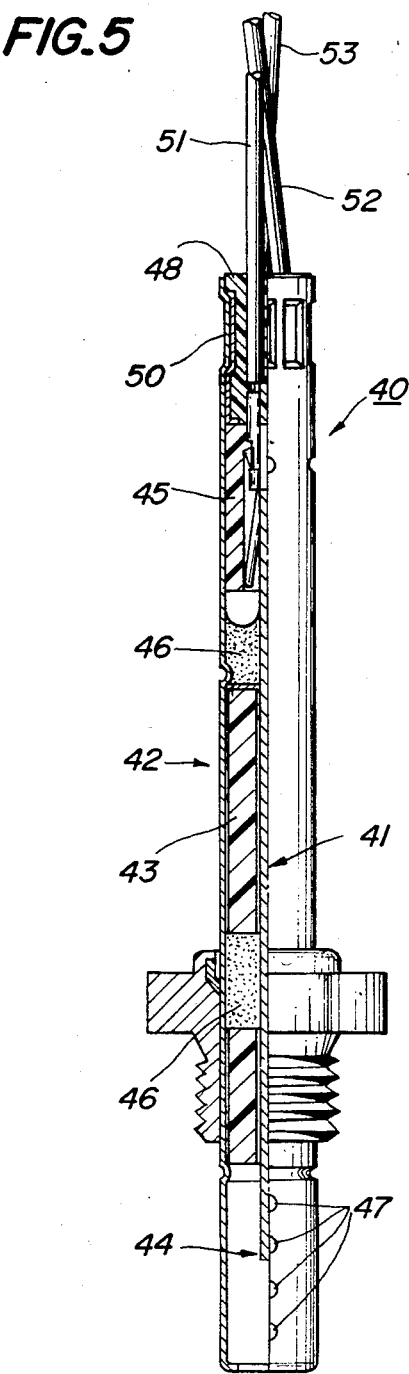
FIG. 5 is a longitudinal crosssectional view of an oxygen sensor showing the whole structure of an oxygen sensor.

Referring to FIG. 1 which shows the first embodiment of a sensor element according to the present invention, a sensor element 1 of an oxygen sensor is illustrate in exploded view. The sensor element 1 is, similar to the aforementioned sensor element 41, accommodate in the protective tube 42, as shown in FIG. 5, to constitute an oxygen sensor 40.

The sensor element 1 is broadly composed of a sensor part 10 and a heater part 20. The sensor part 10 is provided with; a sensor substrate 5 formed by laminating and bonding (bonding is effected by firing) three elongated oxygen ion conductive solid electrolyte plates 2, 3 and 4 consisting mainly of zirconia; a measuring electrode 11 (an electrode which is exposed to a substance to be detected) disposed by printing on an upper right end of an upper solid electrolyte plate 2; and a standard electrode 12 (which is exposed to a standard substance) disposed similarly by printing on an upper right end of a lower solid electrolyte plate 4.

An intermediate solid electrolyte plate 3 has a longitudinal slit 8 extending through the center line of width thereof.

On the upper solid electrolyte plate 2, there is a thin layer or film of a conductive electrode lead 13 which extends in a belt-like fashion from one end of the measuring electrode 11 to the left end of the solid electrolyte plate 2. Similarly, on the upper surface of the solid electrolyte plate 4, there is a thin layer or film of a conductive electrode lead 14 which extends in a belt-like fashion from one end of the standard electrode 12 towards the left end of the solid electrolyte plate 4. The electrode lead 14 is conducted with a belt-like electrode lead 15 applied on the upper solid electrolyte plate 2 via a bend end portion 15' through perforation holes 2a and 3a respectively of the upper and the intermediate solid electrolyte plates 2 and 3.

The solid electrolyte plate 2 with the electrode leads 13 and 15 has on its upper surface a coating of a protective layer 6 of a porous ceramic for protecting the electrode 11 and the electrode leads 13, 15.

The left ends 16, 17 of the electrode leads 13, 15 have on their surfaces connection terminal upper layers 18, 19 formed by applying a conductive coating of a higher metal content than the electrode leads 13, 15 on the left ends 16, 17.

The heater part 20 has a heater 23 consisting of a resistive heating body sandwiched between right ends of two elongated planar insulating ceramic layers 21, 22 which also sandwich similarly two conductive heater leads 28, 29 therebetween which extend in belt-like fashion from the both ends of the heater 23 to the left end of the insulating ceramic layer 21.

The left ends 24, 25 of the heater leads 28, 29 have at their lower surfaces, connection terminals upper layers 26, 27 formed by applying a conductive coating of a higher metal content than the heater leads 28, 29 on the lower surfaces of the left ends 24, 25.

The formed heater part 20 has an integral structure with the sensor part 10 formed by integrally connecting it to the lower surface of the sensor art 10 via an insulating layer 30, so that the insulating ceramic layers 21, 22 and the insulating layer 30 form a part of the sensor substrate 5.

Figure 2:
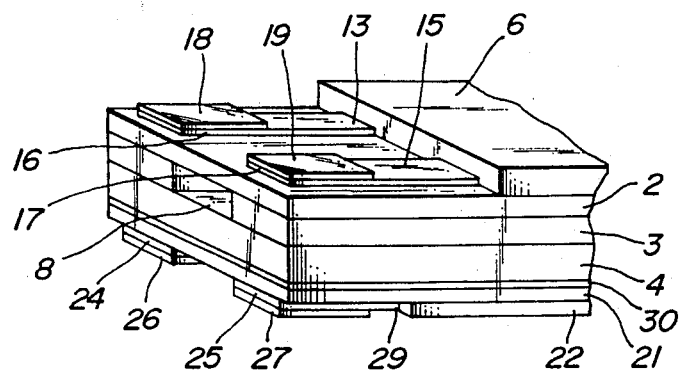
FIG. 2 is a schematic perspective view thereof showing the connection terminals part thereof.

Referring to FIG. 2, the sensor element 41 of a structure as shown in FIG. 1, is engaged or mated with a connector porcelain 45 via the contacting elements 61, 65 as shown in FIGS. 5–8. Contacting elements 61, 65 (the other two elements are omitted in FIG. 2 for simplification, though there are four contacting elements in practice) respectively contact under pressure with upper surfaces of the connection terminals upper layers 18, 19 at the electrodes portion and the connection terminals upper layers 26, 27 at the heater portion.

As described above, the connection terminals upper layers 18, 19, 26, 27 have higher metal contents than the left ends 16, 17 of the electrodes leads 13, 15 and the left ends 24, 25 of the heater leads 28, 29 which form the connection terminals lower layers. Viewed from another aspect, the connection terminals lower layers 16, 17, 24, 25 have a higher ceramic content than the connection terminals upper layers 18, 19, so that they exhibit a stronger bonding force to the solid electrolyte plate 2 or the insulating ceramics layer 21.

For more concretely explaining the foregoing descriptions, an illustrative example of producing the connection terminals upper layers 18, 19, 26, 27, the electrodes leads 13, 14, 15 and the heater leads 28, 29 will be described hereinbelow.

At first, for producing the electrodes leads 13–15 and the heater leads 28, 29, 60 vol% of powder mainly of at least one metal selected from the group consisting of platinum group metals, gold, silver, copper, nickel, chromium, tungsten, molybdenum and a mixture thereof or an alloy of the metals and 40 vol% of stabilized zirconia powder, such as $ZrO_2$ added with 6 mol% of $Y_2O_3$, are added with 4 wt% of ethycellulose and butylcarbitolacetate, kneaded to form a paste, and applied on surfsaces of unfired solid electrolyte plates 2, 4 and unfired insulation ceramic layer 21 by printing to produce the electrode leads 13–15 and the heater leads 28, 29 of an unfired state.

90 vol% of the above-mentioned metal powder and 10 vol% of the stabilized zirconia powder are added with 4 wt% of ethylcellulose and a solvent n-butylcarbitol acetate, kneaded to form a paste, and applied on upper surfaces of the left ends of the paste layers which are planned to form the electrodes leads 13, 15 and the left ends of the paste layers which are planned to form the heater leads 28, 29 by printing, to produce the connection terminals upper layers 18, 19, 26, 27 of an unfired state.

The solid electrolyte plates 2, 4 and the insulation ceramic layers 21 with the pastes applied thereon as described above and the other parts are all laminated, and then fired at 1400° C. for 3 hrs. to accomplish a sensor element the end of which is shown in FIG. 2.

In this embodiment, gold, silver or copper is used mainly as their alloy with other metal of a high melting point or as their mixture with a metal which change to an alloy in the firing process, because their melting points are low. Nickel, chromium, tungsten, molybdenum and copper, etc. are liable to oxidize in an oxidizing atmosphere particularly at a high temperature of about 1400° C., so that they are fired if necessary in a reducing or a neutral atmosphere or fired after coated with a non-oxidizing paste.

This way of preliminarily laminating the connection terminal upper layers and lower layers of paste states and simultaneous firing of the laminated layers is called herein as "method 1". Other than the method 1, the connection terminal upper layers 18, 19, 26, 27, the electrodes leads 13, 14, 15 and the heater leads 28, 29 can be produced in the following "method 2" that the solid electrolyte plates 2, 4 and the insulation ceramics layer 21 are applied with pastes for forming the connection terminals lower layers, i.e., the electrodes leads 16, 17 and the heater leads 28, 29, and then laminated and fired, and thereafter the connection terminal lower layers are applied or coated with pastes for forming the connection terminal upper layers and baked at a temperature, e.g. 1000° C. for 15 min., which is lower than the firing temperature used for forming the connection terminal lower layers.

EXAMPLE 2

Figure 3:
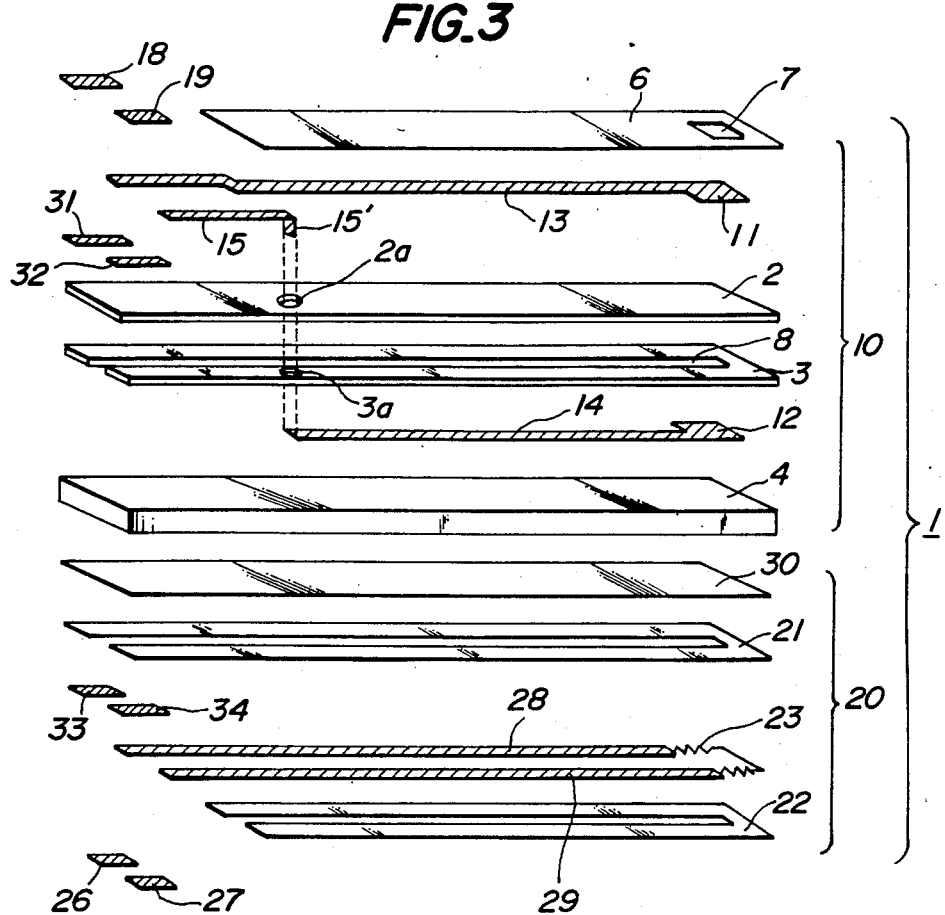
FIG. 3 is a schematic exploded perspective view of a sensor element showing a structure of another embodiment of the present invention.
Figure 4:
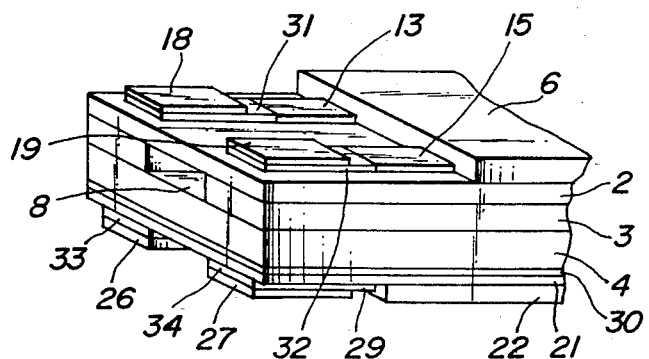
FIG. 4 is a schematic perspective view thereof showing the connection terminals part thereof.

Alternatively, as shown in FIGS. 3–4, the electrode leads 13, 15 and the heater leads 28, 29 may be shorter at their left ends than the solid electrolyte plate 2 and the insulation ceramic layer 21 by a short length, and connection terminal lower layers 31, 32, 33 and 34 of different compositions from those of the leads 13, 15, 28 and 29 of the short length may be formed in contact or integrally therewith, and the connection terminal upper layers 18, 19 26 and 27 may be laminated on the upper surfaces of the connection terminal lower layers 31, 32, 33 and 34 to produce another structure of the sensor element. In this case, if the ceramic content of the connection terminal lower layers 31–34 are larger than the leads 13, 14, 15, 28 and 29, bonding force at the connection terminal portion can be improved greatly without varying resistance values of the leads 13, 14, 15, 28 and 29.

The connection terminal upper layers 18, 19, 26 and 27 and the connection terminal lower layers 31–34 may be laminated in paste shape prior to simultaneous firing of the solid electrolyte plates 2–4, or the upper layers 18, 19, 26 and 27 may be applied on the lower layers 31–34 after firing of the solid electrolyte plates and the lower layers 31–34.

At least one paste layer of a higher metal content than the connection terminal upper layers 18, 19, 26 and 27 may be formed on the upper layers by printing and firing or baking of one or plural times. In another method, one or a plurality of coatings of a least one kind of metal selected from the group consisting of platinum group metal, gold, silver, copper, nickel, chromium, tungsten and molybdenum may be formed on the connection terminal upper layers by a chemical or physical plating process.

EXAMPLE 3

In order to examine the usefulness of the present invention, oxygen sensors according to the present invention and conventional oxygen sensors were prepared. Structure of the oxygen sensors, materials and surface resistance of the connection terminals are respectively shown in the following Table 1.

In Table 1, the structure indicates respectively a drawing of the present invention, and the firing method indicates either of the above explained methods.

The oxygen sensors are assembled to the structure as shown in FIG. 5, and then mounted in an exhaust pipe of a 6 cylinder 2000 cc gasoline internal combustion engine, and tested in an exhaust gas emitted from the engine operating at 4000 rpm at about 800° C. for 800 hrs.

The results are shown in the following Table 2.

TABLE 1

| | | Firing method of connection terminals | Connection terminals lower layer | | | | | | | Connection terminals upper layer | | | | | |
|---|---|---|---|---|---|---|---|---|---|---|---|---|---|---|---|
| | | | Material (vol %) | | | | | | Surface resistance (Ω/sq) | Material (vol %) | | | | | Surface resistance (Ω/sq) |
| Sample No. | Structure | | Pt | Ni | Rh | Y₂O₃—ZrO₂ | Al₂O₃ | Glass | | Pt | Ni | Y₂O₃—ZrO₂ | Al₂O₃ | Glass | |
| Present invention 1 | FIG. 1 | Method 1 | 60 | — | — | 40 | — | — | 0.25 | 90 | — | 10 | — | — | 0.019 |
| 2 | FIG. 1 | Method 1 | 60 | — | — | 40 | — | — | 0.40 | 97 | — | — | 3 | — | 0.010 |
| 3 | FIG. 1 | Method 2 | 60 | — | — | 40 | — | — | 0.33 | 97 | — | — | — | 3 | 0.010 |
| 4 | FIG. 1 | Method 2 | 60 | — | — | 40 | — | — | 0.25 | — | 99 | — | — | 1 | 0.03 |
| 5 | FIG. 3 | Method 1 | 45 | — | — | 50 | 5 | — | 100 | 95 | — | — | 5 | — | 0.015 |
| 6 | FIG. 3 | Method 1 | 40 | — | — | — | 60 | — | 700 | 95 | — | — | 5 | — | 0.015 |
| 7 | FIG. 3 | Method 1 | 40 | — | — | — | 60 | — | 700 | 95 | — | — | 5 | — | 0.015* |
| Reference 8 | | Method 2 | — | 99 | — | — | — | 1 | 0.010 | No upper layer | | | | | |
| 9 | | Method 2 | 97 | — | — | — | — | 3 | 0.020 | | | | | | |
| 10 | | Method 1 | 60 | — | — | 40 | — | — | 0.38 | | | | | | |
| 11 | | Method 1 | — | — | 100 | — | — | — | 0.015 | | | | | | |

*Gold of a thickness of 1 μm was further applied on the upper layer of the Sample No. 7 to decrease the surface resistance to less than 0.01 Ω/sq.

TABLE 2

| Sample No. | | Surface resistance (Ω/sq) | State of the connection |
|---|---|---|---|
| Present invention | 1 | 0.025 | good |
| | 2 | 0.05 | good |
| | 3 | 0.020 | good |
| | 4 | 0.095 | good |
| | 5 | 0.015 | good |
| | 6 | 0.020 | good |
| | 7 | <0.010 | good |
| Reference | 8 | — | Unmeasurable (Peeled at 300 hrs) |
| | 9 | — | Unmeasurable (Peeled at 530 hrs) |
| | 10 | 0.42 | Unstable contact resistance, changed by vibration |
| | 11 | 0.10 | Partial peeling occurred |

As apparent from the above Table 2, the oxygen sensors using the structure according to the present invention has extremely high strength at the connection terminal portions.

Also, from the above results and further various studies, it becomes apparent that the bonding force of the layers can be enhanced such that the peeling-off of the lower layers from sensor substrate is prevented semi-permanently, when the ceramic content of the lowest layer is not less than about 20 vol%, preferably not less than about 35 vol%.

Conversely, when the ceramic content of the connection terminal upper layers is not over than about 20 vol%, preferably about 3-15 vol%, particularly when the upper layers are fired integrally with the sensor substrate, the peeling-off of the upper layers from the sensor substrate or the lower layer can be prevented and the contact resistance between the upper layers and the resilient contacting elements can be reduced.

The connection terminal upper layers and the lower layers have a higher strength when formed by simultaneous firing than when bonded by a late baking.

When a total thickness of the connection terminal part is not less than about 10 μm, preferably not less than about 15 μm, conjunction strength and surface resistance of the connection terminal are improved.

The connection terminal part is not restricted to the two layered structure of the above Examples. It can be a laminated structure of three or more than three layers. In this case, it is more effective if the ceramic content of the layers is made such that each upper layer has a lower ceramic content than its adjacent lower layer, in obtaining an advantageous effect of a strong bonding force and an improved surface resistance. The other conditions are the same as the case of the two-layered structure.

Top surface of the connection terminal part is not restricted to a smooth plane. It can have a recess or protrusion so as to improve an engaging force of the contacting elements in the connector porcelain or connector socket.

The present invention is applicable not only to the above-described oxygen sensor, but also to other sensors of a structure wherein ceramics are used as a base body and conductive connection terminals are arranged on the surfaces of the ceramic body and a connector socket is engaged or mated with the connection terminals via the connecting elements, such as a temperature sensor for high temperatures use, an oxygen sensor using titania $TiO_2$, and the like sensors.

As explained in detail in the foregoing, according to the present invention, electrically conductive connection terminals are made from a multi-layered structure and the lowermost layer contains ceramics or glass, so that a bonding force between the connection terminals and the sensor substrate consisting mainly of ceramics can be improved as well as a bonding force between the multi layers, and peeling-off of the connection terminals from the sensor substrate due to repetition of heating and cooling of the sensor element and friction of the contacting elements of the connector socket against the connection can be prevented.

When the upper layers which are above the lowermost layer have different compositions from a composition of the lowermost layer, for example, each upper layer has more high conductive metal content than a layer just below thereof or each upper layer contains a conductive metal of higher electric conductivity than a conductive metal of a layer just below thereof, the contact resistance between the connection terminals and the contacting element of the connector socket can be decreased.

Through the present invention has been described with specific examples, it is of course apparent to those skilled in the art that various changes and modifications thereof are possible without departing from the broad spirit and aspect of the present invention as hereinafter claimed.

What is claimed is:

1. An electric connection terminal for an oxygen sensor element which includes oxygen sensing ceramics, said electric connection terminal being arranged at one end of a sensor substrate consisting essentially of oxygen sensing ceramics and said one end of the sensor substrate being inserted into a separate connector socket for electrical connection with a contacting element within the connector socket, comprising: at least two layers laminated at said one end of the sensor substrate, a lowermost layer and at least one upper layer above said lowermost layer of said at least two layers comprising different mixtures of a conductive metal and at least one material selected from the group consisting of ceramics and glass, wherein each said at least one upper layer includes an amount of conductive metal which is greater than an amount of conductive metal in a layer immediately below said at least one upper layer, and each of said at least one upper layer and said lowermost layer have different electrical conductivities.

2. An electric connection terminal for an oxygen sensor element as defined in claim 1, wherein the conductive metal comprises at least one metal selected from the group consisting of platinum group elements, gold, silver, copper, nickel, chromium, tungsten and molybdenum.

3. An electric connection terminal for an oxygen sensor element as defined in claim 1, wherein said lowermost layer has a ceramic content of not less than about 20 vol%, and said at least one upper layer has a ceramic content of not greater than about 20 vol%.

4. An electric connection terminal for an oxygen sensor element as defined in claim 1, wherein said lowermost layer is formed by applying a paste for forming the lowermost layer on an unfired sensor substrsate by printing, and firing the unfired sensor substrate with the applied paste at a sintering temperature of the sensor substrate.

5. An electric connection terminal for an oxygen sensor elment as defined in claim 4, wherein said lowermost layer and at least one layer of said at least one upper layer is formed by applying and laminating pastes for forming these layers on the unfired sensor substrate by printing, and firing the unfired sensor substrate with the applied pastes at a sintering temperature of the sensor substrate.

6. An electric connection terminal for an oxygen sensor element as defined in claim 1, wherein said lowermost layer has a ceramic content of not less than about 20 vol%.

7. An electric connection terminal for an oxygen sensor element as defined in claim 1, wherein said lowermost layer has a ceramic content of not less than about 35 vol%.

8. An electric connection terminal for an oxygen sensor element as defined in claim 1, wherein an uppermost layer of said at least one upper layer has a ceramic content of not more than about 20 vol%.

9. An electric connection terminal for an oxygen sensor element as defined in claim 1, wherein an uppermost layer of said at least one upper layer has a ceramic content of about 3–15 vol%.

* * * * *